United States Patent
Andre et al.

(10) Patent No.: US 10,575,737 B2
(45) Date of Patent: Mar. 3, 2020

(54) OPTICAL COHERENT IMAGING MEDICAL DEVICE

(71) Applicant: Novadaq Technologies ULC, Burnaby (CA)

(72) Inventors: Marc Andre, Spiegel b. Bern (CH); Michael Friedrich, Bern (CH); Tyler Thacher, Lausanne (CH); Andrey Naumenko, Ecublens (CH); Romain Farkas, Lausanne (CH)

(73) Assignee: Novadaq Technologies ULC, Burnaby (CA)

(*) Notice: Subject to any disclaimer, the term of this patent is extended or adjusted under 35 U.S.C. 154(b) by 544 days.

(21) Appl. No.: 14/397,290

(22) PCT Filed: Apr. 25, 2013

(86) PCT No.: PCT/IB2013/053271
§ 371 (c)(1),
(2) Date: Oct. 27, 2014

(87) PCT Pub. No.: WO2013/160861
PCT Pub. Date: Oct. 31, 2013

(65) Prior Publication Data
US 2015/0080742 A1 Mar. 19, 2015

(30) Foreign Application Priority Data
Apr. 27, 2012 (WO) .................. PCT/IB2012/052133

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/0059* (2013.01); *A61B 5/0064* (2013.01);
(Continued)

(58) Field of Classification Search
CPC . A61B 5/02007; A61B 5/0059; A61B 5/0064; A61B 5/0066; A61B 5/0261;
(Continued)

(56) References Cited

U.S. PATENT DOCUMENTS 3,796,213 A * 3/1974 Stephens ............ A61B 5/02416
600/479
4,862,894 A 9/1989 Fujii
(Continued)

FOREIGN PATENT DOCUMENTS

CN 101926644 A 12/2010
DE 10 2008 017 390 A1 10/2009
(Continued)

OTHER PUBLICATIONS

Leutenegger, M. et al. "Real-time full field laser Doppler imaging," Biomedical Optics Express, vol. 2, No. 6, p. 1470-1477, May 9, 2011.
(Continued)

*Primary Examiner* — Oommen Jacob
(74) *Attorney, Agent, or Firm* — Morrison & Foerster LLP (57) ABSTRACT

An OCI medical device includes a coherent light source, a light sensor, a first processing unit adapted to calculate OCI Data from the light sensor, a control unit which allows taking or loading of at least one Reference OCI Value, a second processing unit adapted to calculate the Intra-Individual Relative Assessment of the OCI Data of an Imaging Zone and the at least one OCI Reference Value, and display means adapted to show at least one Relative OCI Value. Uses and a method for assessing the blood flow of a body region use OCI imaging and include an Intra-Individual Relative Assessment between OCI Data of the Imaging Zone and at least one Reference OCI Value.

17 Claims, 7 Drawing Sheets

(51) Int. Cl.
    *G06T 7/00*         (2017.01)
    *A61B 5/02*         (2006.01)

(52) U.S. Cl.
    CPC ............ *A61B 5/0066* (2013.01); *A61B 5/445* (2013.01); *A61B 5/742* (2013.01); *G06T 7/0014* (2013.01); *A61B 5/02007* (2013.01); *G06T 2207/10101* (2013.01); *G06T 2207/30104* (2013.01)

(58) Field of Classification Search
    CPC ................ A61B 5/445; A61B 5/742; G06T 2207/10101; G06T 2207/30104; G06T 7/0014
    USPC ................................ 600/477, 476, 407, 479
    See application file for complete search history.

(56) References Cited

U.S. PATENT DOCUMENTS

| | | | |
|---|---|---|---|
| 5,106,387 A * | 4/1992 | Kittrell | A61B 1/00096 600/477 |
| 5,267,016 A | 11/1993 | Meinzer et al. | |
| 5,685,313 A | 11/1997 | Mayevsky | |
| 5,722,405 A * | 3/1998 | Goldberg | A61B 5/0275 600/407 |
| 5,803,914 A * | 9/1998 | Ryals | A61B 5/0275 600/407 |
| 6,045,511 A | 4/2000 | Ott et al. | |
| 6,073,041 A | 6/2000 | Hu et al. | |
| 6,178,340 B1 | 1/2001 | Svetliza | |
| 6,263,227 B1 | 7/2001 | Boggett et al. | |
| 6,485,413 B1 | 11/2002 | Boppart et al. | |
| 6,728,561 B2 | 4/2004 | Smith et al. | |
| 6,970,729 B2 | 11/2005 | Hartmann | |
| 7,113,817 B1 | 9/2006 | Winchester, Jr. et al. | |
| 7,123,363 B2 | 10/2006 | Puttappa et al. | |
| 7,231,243 B2 | 6/2007 | Tearney et al. | |
| 7,483,062 B2 | 1/2009 | Allman et al. | |
| 7,519,212 B2 | 4/2009 | Brady et al. | |
| 8,298,521 B2 | 10/2012 | Schwartz et al. | |
| 8,480,579 B2 | 7/2013 | Serov et al. | |
| 9,066,686 B2 | 6/2015 | Lasser et al. | |
| 9,757,039 B2 | 9/2017 | Lasser et al. | |
| 10,101,571 B2 | 10/2018 | Andre et al. | |
| 10,169,862 B2 | 1/2019 | André et al. | |
| 2002/0052551 A1 | 5/2002 | Sinclair et al. | |
| 2002/0082480 A1 | 6/2002 | Riff et al. | |
| 2003/0011773 A1* | 1/2003 | Dick | A61B 5/0059 356/432 |
| 2003/0023153 A1 | 1/2003 | Izatt et al. | |
| 2003/0118649 A1 | 6/2003 | Gao et al. | |
| 2003/0137669 A1 | 7/2003 | Rollins et al. | |
| 2004/0034294 A1 | 2/2004 | Kimball et al. | |
| 2004/0097805 A1 | 5/2004 | Verand et al. | |
| 2004/0106864 A1* | 6/2004 | Rose | A61B 5/055 600/410 |
| 2004/0107118 A1* | 6/2004 | Harnsberger | G06F 17/24 705/2 |
| 2004/0176701 A1 | 9/2004 | Fujii | |
| 2004/0193035 A1* | 9/2004 | Gharib | A61B 5/0263 600/407 |
| 2004/0225222 A1 | 11/2004 | Zeng et al. | |
| 2005/0008211 A1* | 1/2005 | Xu | G06T 5/009 382/132 |
| 2005/0020892 A1 | 1/2005 | Acosta et al. | |
| 2005/0187477 A1* | 8/2005 | Serov | A61B 5/0261 600/476 |
| 2005/0197559 A1 | 9/2005 | Boese et al. | |
| 2005/0206583 A1 | 9/2005 | Lamelson et al. | |
| 2005/0215889 A1* | 9/2005 | Patterson, II | G06K 9/00 600/436 |
| 2005/0250202 A1* | 11/2005 | March | C12N 5/0667 435/366 |
| 2005/0288565 A1 | 12/2005 | Kerr | |
| 2006/0064024 A1 | 3/2006 | Schnall | |
| 2006/0111620 A1 | 5/2006 | Squilla et al. | |
| 2006/0118742 A1* | 6/2006 | Levenson | A61B 5/0059 250/559.3 |
| 2007/0014489 A1* | 1/2007 | Sun | G06T 7/0012 382/294 |
| 2007/0016078 A1* | 1/2007 | Hoyt | A61B 5/0059 600/476 |
| 2007/0016079 A1* | 1/2007 | Freeman | A61B 5/0059 600/476 |
| 2007/0100245 A1 | 5/2007 | Kashima | |
| 2007/0139613 A1 | 6/2007 | Tanifuji et al. | |
| 2007/0188707 A1 | 8/2007 | Nanjo | |
| 2007/0225606 A1 | 9/2007 | Naghavi et al. | |
| 2007/0239034 A1 | 10/2007 | Knoche et al. | |
| 2007/0291277 A1 | 12/2007 | Everett et al. | |
| 2008/0017787 A1 | 1/2008 | Okawa et al. | |
| 2008/0021329 A1 | 1/2008 | Wood et al. | |
| 2008/0100612 A1 | 5/2008 | Dastmalchi et al. | |
| 2008/0226144 A1* | 9/2008 | Squilla | G06F 19/321 382/128 |
| 2008/0241199 A1 | 10/2008 | Silverman | |
| 2008/0267861 A1* | 10/2008 | Lieu | A61B 6/481 424/1.11 |
| 2008/0294047 A1 | 11/2008 | Kodama et al. | |
| 2009/0054788 A1* | 2/2009 | Hauger | A61B 5/0059 600/476 |
| 2009/0118622 A1 | 5/2009 | Durkin et al. | |
| 2009/0130650 A1 | 5/2009 | Tan et al. | |
| 2009/0192358 A1 | 7/2009 | Jaffer et al. | |
| 2009/0297441 A1* | 12/2009 | Canham | A61K 49/0043 424/1.61 |
| 2010/0049055 A1 | 2/2010 | Freudenberg et al. | |
| 2010/0099992 A1 | 4/2010 | Holschneider et al. | |
| 2010/0113940 A1 | 5/2010 | Sen et al. | |
| 2010/0191541 A1 | 7/2010 | Prokoski | |
| 2011/0013002 A1* | 1/2011 | Thompson | A61B 5/0059 348/77 |
| 2011/0090325 A1* | 4/2011 | Hauger | A61B 5/0261 348/77 |
| 2011/0099031 A1 | 4/2011 | Nair | |
| 2011/0169978 A1* | 7/2011 | Lasser | A61B 3/1233 348/222.1 |
| 2012/0039851 A1* | 2/2012 | Sieveking | A61K 31/56 424/93.1 |
| 2012/0071765 A1 | 3/2012 | Chinnock | |
| 2012/0078113 A1 | 3/2012 | Whitestone et al. | |
| 2012/0195485 A1* | 8/2012 | Matsuba | A61B 5/0263 382/131 |
| 2012/0277559 A1 | 11/2012 | Kohl-Bareis et al. | |
| 2013/0172735 A1 | 7/2013 | Andre et al. | |
| 2013/0223705 A1 | 8/2013 | Ferguson, Jr. et al. | |
| 2013/0245456 A1 | 9/2013 | Ferguson, Jr. et al. | |
| 2013/0296715 A1 | 11/2013 | Lasser et al. | |
| 2014/0049779 A1 | 2/2014 | Tin et al. | |
| 2015/0080742 A1* | 3/2015 | Andre | A61B 5/0059 600/477 |
| 2015/0198797 A1 | 7/2015 | Andre et al. | |
| 2015/0223696 A1* | 8/2015 | Yamanaka | G01N 21/6486 600/473 |
| 2016/0328848 A1 | 11/2016 | Andre et al. | |
| 2016/0367145 A1 | 12/2016 | Lasser et al. | |
| 2018/0098702 A1 | 4/2018 | Lasser et al. | |

FOREIGN PATENT DOCUMENTS

| | | |
|---|---|---|
| EP | 0763998 A1 | 3/1997 |
| EP | 1 210 910 A1 | 6/2002 |
| EP | 1241979 A1 | 9/2002 |
| EP | 1 982 645 A1 | 10/2008 |
| JP | S63-214238 A | 9/1988 |
| JP | H10-508763 A | 9/1998 |
| JP | H11-142748 A | 5/1999 |
| JP | 2003-516795 A | 5/2003 |
| JP | 2003-527700 A | 9/2003 |
| JP | 2004-267308 A | 9/2004 |

(56) References Cited

FOREIGN PATENT DOCUMENTS

| JP | 2005-515818 A | 6/2005 |
|---|---|---|
| JP | 2005-532393 A | 10/2005 |
| JP | 2006-180926 A | 7/2006 |
| JP | 2007-315827 A | 12/2007 |
| JP | 2008-142355 A | 6/2008 |
| JP | 2008-541891 A | 11/2008 |
| JP | 2008-289870 A | 12/2008 |
| JP | 2010-532699 A | 10/2010 |
| JP | 2011-027895 A | 2/2011 |
| JP | 2012-113191 A | 6/2012 |
| WO | WO-1995/32664 A1 | 12/1995 |
| WO | WO-2001/43628 A1 | 6/2001 |
| WO | WO-03/063677 A1 | 8/2003 |
| WO | WO 2005/099572 A1 | 10/2005 |
| WO | WO-2005/099582 A1 | 10/2005 |
| WO | WO-2006/111836 A1 | 10/2006 |
| WO | WO-2006/111909 A1 | 10/2006 |
| WO | WO-2006/121984 A2 | 11/2006 |
| WO | WO-2006/121984 A3 | 11/2006 |
| WO | WO-2007/148073 A1 | 12/2007 |
| WO | WO-2009/028136 A1 | 3/2009 |
| WO | WO-2009/142641 A1 | 11/2009 |
| WO | WO-2010/004365 A1 | 1/2010 |
| WO | WO-2011/084528 A1 | 7/2011 |
| WO | WO-2011/117779 A2 | 9/2011 |
| WO | WO-2011/117779 A3 | 9/2011 |
| WO | WO-2013/160861 A1 | 10/2013 |
| WO | WO-2014/009859 A2 | 1/2014 |
| WO | WO-2014/009859 A3 | 1/2014 |

OTHER PUBLICATIONS

International Search Report issued in International Patent Application No. PCT/IB2013/053271 dated Sep. 11, 2013.
Briers, J.D. (Nov. 2001). "Laser Doppler, Speckle and Related Techniques for Blood Perfusion Mapping and Imaging," *Physiol. Meas.* 22(4):R35-R66.
Dyck, R.H. et al. (1968). "Integrated Arrays of Silicon Photodetectors for Image Sensing," *IEEE Transactions on Electron Devices* 15(4):196-202.
Jones, P.B. et al. (Jul.-Aug. 2008) "Simultaneous Multispectral Reflectance Imaging and Laser Speckle Flowmetry of Cerebral Blood Flow and Oxygen Metabolism in Focal Celebral Ischemia," *J. Biomed Opt.* 13(4):04407, twenty three pages.
Jeong et al. (Feb. 2006). "Functional Optical Coherence Imaging of Tumor Response to a Metabolic Electron Transport Inhibitor," *Proceedings of the SPIE* 6079(1):60790K-1-60790K-8.
Kalchenko, V. et al. (Feb. 10, 2001). "Multi-modal Diagnostic Approach for Functional Imaging of Tumor Vascular Network and Blood Microcirculation," *Proc. of SPIE* 7898(1):1-7.
Michelson, G. et al. (Jun. 2002). "Flickering Light Increases Retinal Blood Flow," *Database Biosis [Online] Biosciences Information Service* 22(3):336-343.
Schmeisser, E.T. et al. (May 2003). "Modification of the Heidelberg Retinal Flowmeter to Record Pattern and Flicker Induced Blood Flow Changes", *Documenta Ophthalmologica* 106(3):257-263.
Senarathna, J. et al. (Jan. 28, 2013). "Laser Speckle Contrast Imaging: Theory, Instrumentation, and Application," *IEEE Reviews in Biomedical Engineering* vol. 6:99-110.
Serov, A. et al. (Oct. 3, 2001). "Speckles in Laser Doppler Blood Flowmetry," *Proceedings of the SPIE* 4242:306-318.
Serov, A. (2002). "Novel Instruments for Remote and Direct-Contact Laser Doppler Perfusion Imaging and Monitoring," Ph.D. Thesis, University of Twente, 128 pages.
Sun, X. et al. (May 14, 2011). "Simultaneous Monitoring of Intracellular PH Changes and Hemodynamic Response During Cortical Spreading Depression by Fluorescence-Corrected Multimodal Optical Imaging," *Neuroimage* 57(3):873-884.
Canadian Office Action dated Nov. 10, 2016 for Canadian Patent Application No. 2,914,780 filed on Jul. 10, 2012, four pages.
Canadian Office Action dated Oct. 12, 2016 for Canadian Application No. 2,909,914 filed on Apr. 25, 2013, four pages.
European Communication pursuant to Article 94(3) EPC dated Nov. 25, 2016 for European Application No. 08789265.9, filed on Feb. 8, 2011, five pages.
European Office Action dated Aug. 19, 2008, for EP Application No. 06 744 526.2, filed on Apr. 20, 2006, three pages.
European Office Action dated Dec. 4, 2012, for EP Application No. 06 744 526.2, filed on Apr. 20, 2006, four pages.
European Office Action dated Jul. 1, 2010, for EP Application No. 06 744 526.2, filed on Apr. 20, 2006, five pages.
International Preliminary Report on Patentability (IPRP) (Chapter I) for PCT/IB2008/052787, dated Jan. 11, 2011.
International Search and Written Opinion dated Jul. 15, 2016 for PCT Application No. PCT/CA2016/050526, filed on May 6, 2016, eight pages.
International Search Report dated Aug. 14, 2006, for PCT Patent Application No. PCT/IB2006/000940, filed on Apr. 20, 2006, three pages.
International Search Report dated Aug. 14, 2006, for PCT Patent Application No. PCT/IB2006/051167, filed on Apr. 13, 2006, three pages.
International Search Report dated Jan. 3, 2014, for PCT Application No. PCT/IB2013/055517, filed on Jul. 5, 2013, six pages.
International Search Report dated Mar. 24, 2009, for PCT Application No. PCT/IB2008/052787, filed on Jul. 10, 2008, five pages.
International Search Report dated Nov. 23, 2011, for PCT Application No. PCT/IB2011/051098, filed on Mar. 16, 2011, seven pages.
Japanese Office Action dated Feb. 1, 2016, for Japanese Patent Application No. 2015-521112, filed Jul. 5, 2013, twelve pages.
Japanese Office Action dated Oct. 30, 2015, for Japanese Patent Application No. 2015-507652, filed on Apr. 25, 2013, nine pages.
U.S. Final Office Action dated Apr. 4, 2016, for U.S. Appl. No. 13/636,268, filed Mar. 4, 2013, thirteen pages.
U.S. Final Office Action dated Aug. 18, 2011, for U.S. Appl. No. 11/912,224, filed Oct. 22, 2007, five pages.
U.S. Final Office Action dated Aug. 23, 2013, for U.S. Appl. No. 13/057,593, filed Mar. 21, 2011, fourteen pages.
U.S. Final Office Action dated Dec. 16, 2016 for U.S. Appl. No. 13/935,947, filed on Jul. 5, 2013, twenty three pages.
U.S. Final Office Action dated Feb. 20, 2015, for U.S. Appl. No. 13/636,268, filed Mar. 4, 2013, seventeen pages.
U.S. Final Office Action dated May 19, 2017, for U.S. Appl. No. 14/413,106, filed Jan. 6, 2015, twelve pages.
U.S. Final Office Action dated Nov. 29, 2012, for U.S. Appl. No. 11/912,224, filed Oct. 22, 2007, eight pages.
U.S. Final Office Action dated Oct. 6, 2015, for U.S. Appl. No. 13/935,947, filed Jul. 5, 2013, fifteen pages.
U.S. Final Office Action dated Sep. 26, 2016, for U.S. Appl. No. 13/636,268, filed Mar. 4, 2013, fifteen pages.
U.S. Non-Final Office Action dated Apr. 29, 2016, for U.S. Appl. No. 13/935,947, filed Jul. 5, 2013, twenty pages.
U.S. Non-Final Office Action dated Aug. 11, 2014, for U.S. Appl. No. 13/057,593, filed Mar. 21, 2011, nineteen pages.
U.S. Non-Final Office Action dated Dec. 17, 2012, for U.S. Appl. No. 13/057,593, filed Mar. 21, 2011, fourteen pages.
U.S. Non-Final Office Action dated Jan. 16, 2015, for U.S. Appl. No. 13/935,947, filed Jul. 5, 2013, seven pages.
U.S. Non-Final Office Action dated Mar. 14, 2012, for U.S. Appl. No. 11/912,224, filed Oct. 22, 2007, seven pages.
U.S. Non-Final Office Action dated Mar. 8, 2011, for U.S. Appl. No. 11/912,224, filed Oct. 22, 2007, nine pages.
U.S. Non-Final Office Action dated Nov. 10, 2016, for U.S. Appl. No. 14/413,106, filed Jan. 6, 2015, twelve pages.
U.S. Non-Final Office Action dated Nov. 3, 2015, for U.S. Appl. No. 13/636,268, filed Mar. 4, 2013, fourteen pages.
U.S. Non-Final Office Action dated Sep. 29, 2014, for U.S. Appl. No. 13/636,268, filed Mar. 4, 2013, ten pages.
U.S. Non-Final Office Action dated Feb. 1, 2017, for U.S. Appl. No. 14/753,997, filed on Jun. 29, 2015, seven pages.
U.S. Notice of Allowance dated Feb. 27, 2015, for U.S. Appl. No. 13/057,593, filed Mar. 21, 2011, eight pages.

(56) References Cited

OTHER PUBLICATIONS

U.S. Notice of Allowance dated May 9, 2013, for U.S. Appl. No. 11/912,224, filed Oct. 22, 2007, six pages.
U.S. Notice of Allowance dated May 5, 2017, for U.S. Appl. No. 14/753,997, filed Jun. 29, 2015, five pages.
Written Opinion of the International Searching Authority dated Aug. 14, 2006, for PCT Patent Application No. PCT/IB2006/000940, filed on Apr. 20, 2006, seven pages.
Written Opinion of the International Searching Authority dated Aug. 14, 2006, for PCT Patent Application No. PCT/IB2006/051167, filed on Apr. 13, 2006, seven pages.
Written Opinion of the International Searching Authority dated Mar. 24, 2009, for PCT Application No. PCT/IB2008/052787, filed on Jul. 10, 2008, nine pages.
Written Opinion of the International Searching Authority dated Sep. 11, 2013, for PCT Application No. PCT/IB2013/053271, filed on Apr. 25, 2013, seven pages.
Written Opinion of the International Searching Authority dated Nov. 23, 2011, for PCT Application No. PCT/IB2011/051098, filed on Mar. 16, 2011, ten pages.
Written Opinion of the International Searching Authority dated Jan. 3, 2014, for PCT Application No. PCT/IB2013/055517, filed on Jul. 5, 2013, ten pages.
Golpayegani, G.N. et al. (May 16, 2008). "Laser Doppler and Laser Speckle Techniques for Blood flow Measurement," *2nd International Conference on Bioinformatics and Biomedical Engineering* pp. 1555-1560.
Hillman, E.M. (Sep.-Oct. 2007). "Optical Brain Imaging in Vivo: Techniques and Applications from Animal to Man," *J Biomed Opt.* 12(5):051402, total of 49 pages.
Canadian Notice of Allowance dated Sep. 22, 2017, for Canadian Patent Application No. 2,909,914, filed on Oct. 20, 2015, one page.
Canadian Notice of Allowance dated Oct. 27, 2017, for Canadian Patent Application No. 2,914,780, filed on Dec. 8, 2015, one page.
European Communication Pursuant to Rule 164(2)(b) and Article 94(3) EPC dated Jun. 20, 2017, for EP Application No. 11718157.8, filed on Mar. 16, 2011, eight pages.
International Preliminary Report on Patentability (IPRP) (Chapter I) dated Nov. 16, 2017 for PCT Application No. PCT/CA2016/050526, filed on May 6, 2016, six pages.
Japanese Office Action dated Jul. 7, 2017, for Japanese Application No. 2016-199363, filed on Oct. 7, 2016, eight pages.
U.S. Non Final Office Action dated Sep. 29, 2017 for U.S. Appl. No. 13/935,947, filed Jul. 5, 2013, twenty eight pages.
U.S. Non-Final Office Action dated Sep. 21, 2017, for U.S. Appl. No. 14/413,106, filed Jan. 6, 2015, twelve pages.
U.S. Non-Final Office Action dated Feb. 14, 2017, for U.S. Appl. No. 13/636,268, filed Mar. 4, 2013, thirteen pages.
U.S. Non-Final Office Action dated Dec. 14, 2017, for U.S. Appl. No. 15/148,959, filed on May 6, 2016, twelve pages.
U.S. Supplemental Notice of Allowability dated May 24, 2017, for U.S. Appl. No. 14/753,997, filed Jun. 29, 2015, three pages.
European Communication pursuant to Article 94(3) EPC dated Mar. 15, 2018 for European Application No. 11718157.8, filed on Mar. 16, 2011, four pages.
European Communication under Rule 71(3) EPC Intention to Grant dated Apr. 25, 2018 for EP Application No. 08789265.9, filed on Feb. 8, 2011, seven pages.
Japanese Notice of Allowance dated Jan. 12, 2018 for Japanese patent Application No. 2016-199363 filed on Oct. 7, 2016, six pages.
U.S. Final Office Action dated Apr. 25, 2018, for U.S. Appl. No. 13/935,947, filed Jul. 5, 2013, thirty three pages.
U.S. Final Office Action dated Mar. 27, 2018, for U.S. Appl. No. 14/413,106, filed Jan. 6, 2015, thirteen pages.
U.S. Non-Final Office Action dated Mar. 5, 2018, for U.S. Appl. No. 13/636,268, filed Mar. 4, 2013, seventeen pages.
European Communication Pursuant to Article 94(3) EPC dated Feb. 7, 2019, for EP Application No. 11718157.8, filed on Mar. 16, 2011, four pages.
European Communication Under Rule 71(3) EPC dated Sep. 21, 2018 for European Application No. 08789265.9, filed on Feb. 8, 2011, seven pages.
European Office Action dated Dec. 11, 2018 for EP Application No. 13773842.3 filed on Dec. 9, 2014, five pages.
Japanese Office Action dated Oct. 9, 2018, for Japanese Application No. 2017-558505, filed on Nov. 7, 2017, seven pages.
U.S. Final Office Action dated Jul. 20, 2018, for U.S. Appl. No. 15/148,959, filed on May 6, 2016, nine pages.
U.S. Non-Final Office Action dated Dec. 11, 2018, for U.S. Appl. No. 15/663,313, filed Jul. 28, 2017, seven pages.
U.S. Notice of Allowance dated Aug. 13, 2018, for U.S. Appl. No. 14/413,106, filed Jan. 6, 2015, seven pages.
U.S. Notice of Allowance dated Sep. 25, 2018, for U.S. Appl. No. 15/148,959, filed on May 6, 2016, seven pages.
Kalchenko, V. et al. (Feb. 6, 2008). "Combined Use of Fluorescent and Dynamic Light Scattering Imaging for Applications in Vascular Biology," *Proceedings of SPIE* vol. 6855, 9 pages.
Kang, Y. et al. (Jan. 26, 2009). "Quantitative Analysis of Peripheral Tissue Perfusion Using Spatiotemporal Molecular Dynamics," *PLOS One* 4(1):e4275, 11 pages.
Canadian Office Action dated Jun. 6, 2019, for Canadian Patent Application No. 2,914,780, filed on Dec. 8, 2015, three pages.
European Notice of Allowance dated Feb. 7, 2019 for EP Application No. 08789265.9, filed on Feb. 8, 2011, two pages.
European Office Action dated Apr. 9, 2019 for EP Application No. 13773842.3 filed on Dec. 9, 2014, thirteen pages.
European Search Report dated Oct. 9, 2018 for EP Application No. 16789002.9 filed on Dec. 7, 2017, eight pages.
U.S. Final Office Action dated Apr. 2, 2019, for U.S. Appl. No. 15/663,313, filed Jul. 28, 2017, six pages.

\* cited by examiner

← Site for comparison →

| | Hand Palm | Hand Top | Forearm | Upper Arm | Thorax | Head | Abdomen | Thigh | Lower Leg | Foot |
|---|---|---|---|---|---|---|---|---|---|---|
| Hand Palm | NA | 46% | 51% | 78% * | NS | NS | NS | 74% | 57% | 44% |
| Hand Top | 218% | NA | NS | 169% | 205% | 247% | 214% | 161% | NS | NS |
| Forearm | 195% | NS | NA | 151% | 184% | 221% | 191% | 144% | NS | NS |
| Upper Arm | 129% * | 59% | 66% | NA | 121% * | 146% | 127% | NS | 74% | 56% |
| Thorax | NS | 49% | 54% | 82% | NA | NS | 104% | 78% | 61% | 46% |
| Forehead | NS | 41% | 45% | 68% | NS | NA | NS | 65% | 51% | 39% |
| Abdomen | NS | 47% | 52% | 79% | NS | NS | NA | 75% | 59% | 45% |
| Thigh | 136% | 62% | 70% | NS | 128% | 154% | 133% | NA | 78% * | 59% |
| Lower Leg | 174% | NS | NS | 135% | 164% | 197% | 171% | 128% | NA | NS |
| Foot | 229% | NS | NS | 177% | 215% | 259% | 224% | 169% | NS | NA |

(Reference axis)

OPTICAL COHERENT IMAGING MEDICAL DEVICE

FIELD OF INVENTION

The invention relates to perfusion visualization using Optical Coherent Imaging (OCI) in the medical field.

DEFINITIONS

Optical Coherent Imaging (OCI): A contactless and non-invasive medical imaging modality utilizing the physical properties, and in particular the coherence properties, of light to record, measure, visualize and/or assess physiological and non-physiological flow properties, and in particular blood flow properties, in a selected tissue and/or body area of interest. OCI systems comprise of at least, but are not limited to: a coherent light source, a light acquisition unit, an image and data processing and device control unit, and means to visualize and represent the flow information. Specific implementations of OCI include, but are not limited to: Laser Doppler Imaging (LDI), Laser Doppler Spectroscopic Imaging (LDSI), Laser Speckle Imaging (LSI), Laser Speckle Contrast Analysis (LASCA), Functional Optical Coherent Imaging (fOCI, as for instance disclosed in WO2010/004364), Optical Coherence Tomography (OCT), and Optical Coherence Microscopy (OCM).

OCI Map: Any digital two- or three-dimensional dataset generated by OCI or by any function of one or several OCI Maps. Examples are, but are not limited to, (1) a perfusion map generated by LDI, (2) a time- and/or spatially averaged perfusion map generated by LDI, or (3) the element-by-element ratio of two perfusion maps generated by LDI. Two-dimensional (2D) OCI Maps can be represented as an image with x-y coordinates. Three-dimensional OCI Maps can be reduced to 2D OCI Maps using projection, slicing or other appropriate methods and algorithms.

OCI Value: A single element or pixel of an OCI Map, an ROI Value or a function of a set of OCI Values.

Absolute OCI Value: An OCI Value with an arbitrary or standardized unit.

Reference OCI Value: An OCI Value used as reference with respect to another OCI Value.

Relative OCI Value: An OCI Value which is calculated with respect to a Reference OCI Value.

Absolute OCI Map: An OCI Map consisting of Absolute OCI Values.

Relative OCI Map: An OCI Map consisting of Relative OCI Values.

OCI Data: Refers to one or several OCI Maps and/or one or several OCI Values.

Reference Zone: Body area used to calculate the Reference OCI Value.

Imaging Zone: Body area from which OCI Maps are calculated. This applies both to Absolute ROI Maps as well as Relative ROI Maps, and is usually meant to be the body area currently being examined with the OCI system.

Region of Interest (ROI): An area within an OCI Map.

ROI Value: An absolute or relative value determined as function of the OCI Values within an ROI.

Perfusion: Delivery of blood to a capillary bed in a biological tissue. Perfusion in general is considered as a property of the blood flow in the microcirculation.

Absolute Mode: Method where the output is Absolute OCI Data.

Relative Mode: Method where a comparison between one or multiple Reference OCI Value and one or multiple OCI Values in the Imaging Zone is performed.

Intra-Individual Relative Assessment: Case of Relative Mode where the Reference Zone and the Imaging Zone are on the same patient.

Body Mapping Factor: The relationship of two OCI Values of distinct body areas of the same patient that is statistically significant for the said pair of body areas and a given Population Group and Clinical Context.

Body Mapping Factor Table: A set of Body Mapping Factors for a Population Group and a defined Clinical Context.

Body Mapping Factor Database: A collection of Body Mapping Factor Tables for at least one Population Group and at least one Clinical Context.

Population Group: A group of patients to whom the same Body Mapping Factors can be applied within a defined Clinical Context.

Clinical Context: Clinical use cases to which the same Body Mapping Factor can be applied within a defined Population Group.

Field Programmable Gate Array (FPGA): An integrated circuit with configurable digital logic circuits.

Real-Time: applied to visualization is a reasonable visualization update frequency with short latency so that the user can have an immediate feedback from any change of the observed area or the movement of the camera.

Colormap: A look-up table or function which maps values to colors.

Indexed Map: A map which is built of discrete numbers (e.g. Integer) to be used as indexed image which can be converted to a color image by using a Colormap.

Display or Screen: An element or elements of a human machine interface. Both terms shall be used as synonyms and not refer to specific technologies.

Human Machine Interface: Any suitable means to show results to the user and optionally to accept input from the user.

STATE OF THE ART

Optical Coherent Imaging is a non-contact imaging modality utilizing, to a large extent, the physical properties and in particular the coherence properties of light. This imaging modality integrates a detector technology, combined with an appropriate coherent light source and an image-processing unit for extracting the flow characteristics of the observed body area of interest. Thereby, it facilitates the diagnosis or observation of multiple diseases and disorders such as peripheral vascular diseases, skin irritations, diabetes, burns, organ transplants, tissue grafts and even functional brain imaging. This method is non-invasive because it involves no physical contact; therefore risk of infection and discomfort are greatly avoided.

Sub-classes of OCI include, but are not limited to: Laser Doppler Imaging (LDI), Laser Doppler Spectroscopic Imaging (LDSI), Laser Speckle Imaging (LSI), Laser Speckle Contrast Analysis (LASCA), Functional Optical Coherent Imaging (fOCI, as for instance disclosed in WO2010/004364), Optical Coherence Tomography (OCT), and Optical Coherence Microscopy (OCM).

All OCI systems known to measure the micro vascular flow provide Absolute OCI Values. The unit of the Absolute OCI Values is differently calibrated and defined. Most systems refer to arbitrary perfusion units (apu). OCI systems units are normally proportional to the Perfusion, velocity, concentration and/or other property of blood flow. In LDI Perfusion is considered as the product of the average velocity and concentration of blood. In the present document Perfusion shall be used as example for an OCI Value and be exchangeable with any other type of OCI Value.

The OCI map is usually shown with a Colormap. The Colormap maps the OCI Value to a color. Such mapping often uses several colors for different value intervals and usually gradients between the colors. The Colormap often doesn't cover the full dynamic range of the OCI values. The Colormap is scaled to represent a range (usually zero to specific OCI value) with its full color range. Higher values are saturated. The scaling is, depending on existing devices, fixed or manually adjustable with discrete intervals.

Levels of Absolute Perfusion vary greatly at different regions of the body and among individuals even when carefully stratifying patient groups by age, sex, BMI and the presence of microcirculatory disorders. It is therefore difficult to set thresholds for Absolute Perfusion for specific assessments such as burns depth assessment or to define normal Absolute Perfusion values as these values vary between individuals.

GENERAL DESCRIPTION OF THE INVENTION

It was surprisingly found that in applications, such as the assessment of burns healing potential, flap design and flap reperfusion assessment, wound healing, ulcers, bedsores, diabetes, systemic vascular issues, or rheumatology, it is more advantageous to work in Relative Mode, with comparison of OCI Values between different sites on the same patient. Assessments (e.g. thresholds, gold standards) are then done using relative measurements, i.e. if the Perfusion of a burn wound is higher/lower than an adjacent region or if the Perfusion of a flap is lower than neighboring tissue. This method compares OCI Data (OCI Value or OCI Map) with a Reference OCI Value on the same patient and is also referred to Intra-Individual Relative Assessment.

The invention therefore relates to a device, a method and uses as defined in the claims.

Furthermore, the inventors have surprisingly found, and then demonstrated, that the ratio of Absolute Perfusion between certain body regions among individuals constitutes a meaningful feature for the assessments mentioned previously. It is therefore possible to improve the invention in developing a Body Mapping methodology which is based on intra-individual Perfusion ratios. Many intra-individual Perfusion ratios between body regions have been found which are highly reproducible and hold constant among stratified patient populations. It is therefore possible to build a database of those ratios, which is called Body Mapping Factor Table in the present document.

In some circumstances it is difficult to compare the Perfusion with a nearby or corresponding body part, for example in severe burns where a large area of the body is burned. In those situations it becomes necessary to use a reference from a body part which is different than the burned region when working with Intra-Individual Relative Assessment. By mapping human cutaneous perfusion, correction factors (Body Mapping Factors) can be developed allowing the use of references from anywhere on the body. The intra-individual ratio is corrected by the Body Mapping Factor.

The same body mapping can also be useful for assessing Perfusion in applications with systemic vascular issues such as ulcers, diabetes, extremity perfusion or systemic vascular disease. In such applications it is possible to use the known Body Mapping Factor and the Intra-Individual Relative Assessment to set a standard Perfusion level which is then compared to the real measured level.

The mentioned methods are developed with laser Doppler imaging, but they work with all optical coherent imaging (OCI) technologies for visualizing the blood flow. This includes OCT based perfusion imaging and laser speckle imaging technologies which are called Laser Speckle Contrast Analysis (LASCA) or Laser Speckle Imaging (LSI). The methods can also work with non-OCI methods for detecting the blood flow such as fluorescence imaging (with Indocyanine green IGC or other fluorescent dye), acoustic Doppler measurements or thermography assuming that these systems provide a value which is comparable to an OCI Value (proportional to a blood flow property such as perfusion, velocity and/or concentration). In that case the result of such non-OCI method can be considered as OCI Data.

DETAILED DESCRIPTION OF THE INVENTION

The invention will be better understood below with a more detailed description illustrated by non-limitative examples.

RELATIVE MODE

The present invention describes a novel approach to OCI. Current OCI systems generate Absolute OCI Maps and Absolute OCI Values. The novel OCI system allows for comparing OCI Maps and OCI Values which creates Relative OCI Maps or Relative OCI Values. Usually the comparison is done on the same patient, in such case this method is referred to Intra-Individual Relative Assessment. It is possible to compare OCI Maps and OCI Values with nearby body area, across the body or over (short or extended) time. This new approach does not only address previously mentioned limitations of the traditional OCI systems which only work in Absolute Mode, but it also expands the clinical scope of OCI.

The basic principle is to compare the OCI Maps and OCI Values to a Reference OCI Value. The Reference OCI Value is usually previously recorded by taking the ROI Value of a relevant zone (Reference Zone). The ROI can have any shape and position within the OCI map, but centered circular or rectangular ROI is a good choice. Also, the size of the ROI can differ for clinical applications and is possibly selectable by the user. The ROI Value is calculated from the OCI Map by statistical functions such as spatial mean, spatial median or any other function to determine a representative value of all values within the ROI. The Reference OCI Value can also be taken from several subsequent frames, several ROI and/or be filtered. Often it is useful to filter the OCI Reference Value such that pulsation of the heart beat and noise is removed. Such removal filter could be a long-time time average, some wavelet based filter, component analysis/decomposition, or any other reasonable filter. It is also possible to acquire the Reference OCI Value with other means or to load it from a file.

The result of the comparison is Relative OCI Data (Relative OCI Maps or Relative OCI Values). This Data is a function of the OCI Map or OCI Value from the Imaging Zone (value$_{absolute}$) and the Reference OCI Value (value$_{reference}$). The general relationship is shown in Equation (1). Often the function is calculated as ratio of the OCI Value and the Reference OCI Value as shown in Equation (2).

$$\text{value}_{rel}(x, y) = f(\text{value}_{absolute}(x, y), \text{value}_{reference}) \tag{1}$$

$$\text{value}_{rel}(x, y) = \frac{\text{value}_{absolute}(x, y)}{\text{value}_{reference}} \tag{2}$$

value$_{absolute}$ and value$_{reference}$ correspond to the Absolute OCI Values. The resulting value$_{rel}$(x, y) as shown in Equation (2) has no unit and is often represented as percentage value (thus multiplied by 100%). It can also be shown as factor or as its inverse. In other definition of f(value$_{absolute}$(x, y), value$_{reference}$), value$_{rel}$(x, y) can also have a Perfusion Unit. This is for example the case if the simple difference between the Reference OCI Value and the Absolute OCI Value in the Imaging Zone is calculated.

The calculation (1) is normally repeated for each pixel in the OCI Map being assessed. Additional filters such as time averaging, time median, spatial filters and others can be applied before or after the Relative OCI Map calculation. It is also possible to use multiple OCI Reference Values to calculate the Relative OCI Values or Maps.

Dynamic Range

The Relative OCI Value has a different dynamic range than the Absolute OCI Value. In Absolute Mode, often the Absolute OCI Value is a scaled extract from the full dynamic range of the system. Such OCI Value eventually saturates in high-perfused areas. This has to be overcome for calculation of the Relative Map because the user would not recognize such saturation. In order to calculate correct values, the full dynamic range for value$_{absolute}$ should be used while keeping a good resolution in low-perfusion region. In the preferred embodiment the Relative Map is directly calculated in the FPGA using full 16-bit dynamic range of the LDI signal.

Indexed Map

Figure 2A:
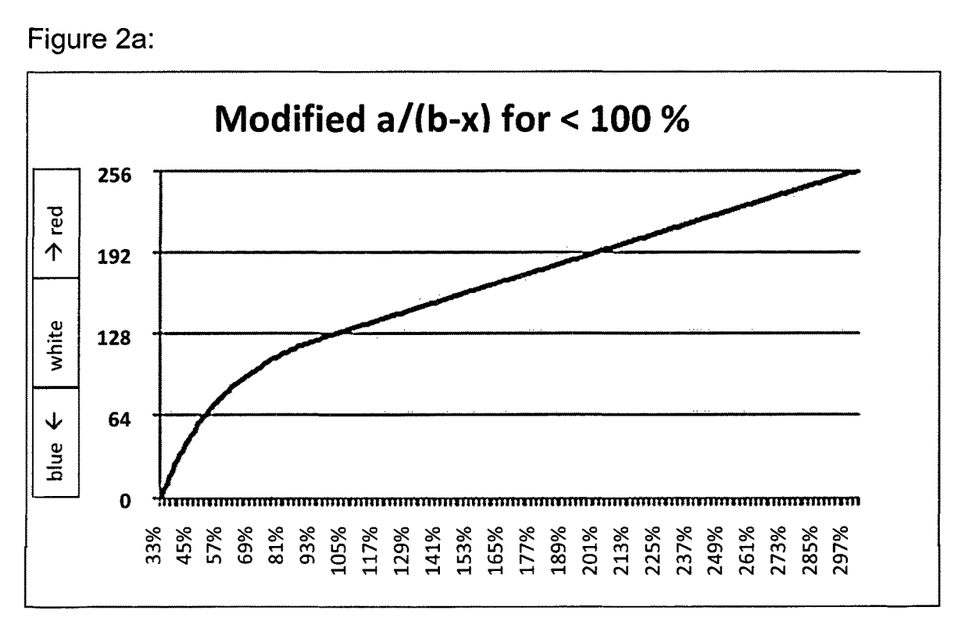
FIG. 2*a*: Mapping of the Relative Perfusion Values (in the range from 33% to 300%) to integer values used to look-up the corresponding colors. The mapping function is divided into two segments: a/(b−x) from 33% (0) to 100% (127), and linear from 100% (128) to 300% (255).
Figure 2B:
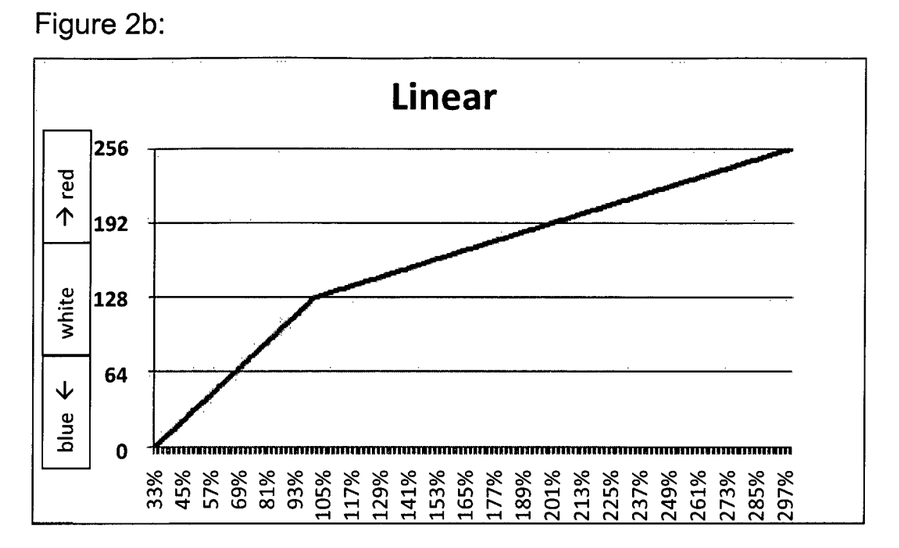
FIG. 2*b*: Mapping of the Relative Perfusion Values (in the range from 33% to 300%) to integer values used to look-up the corresponding colors. The mapping function is divided into two segments: Linear from 33% (0) to 100% (127), and linear from 100% (128) to 300% (255).
Figure 3:
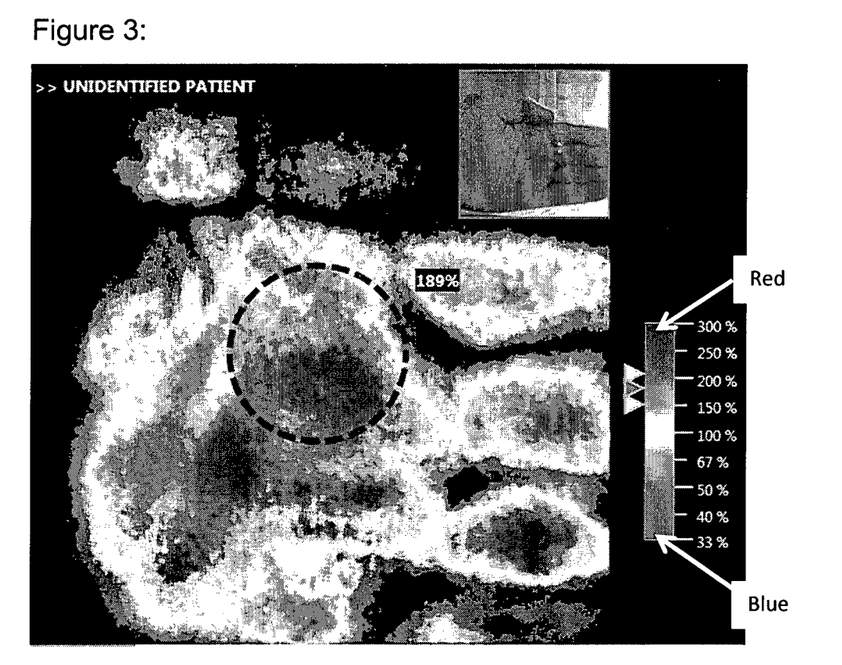
FIG. 3: Example of a Colormap where the Relative Perfusion Values (of a left hand) between 33% and 300% are displayed (from blue via white to red), while the other Relative Perfusion Values are not displayed (set to black).
Figure 4A:
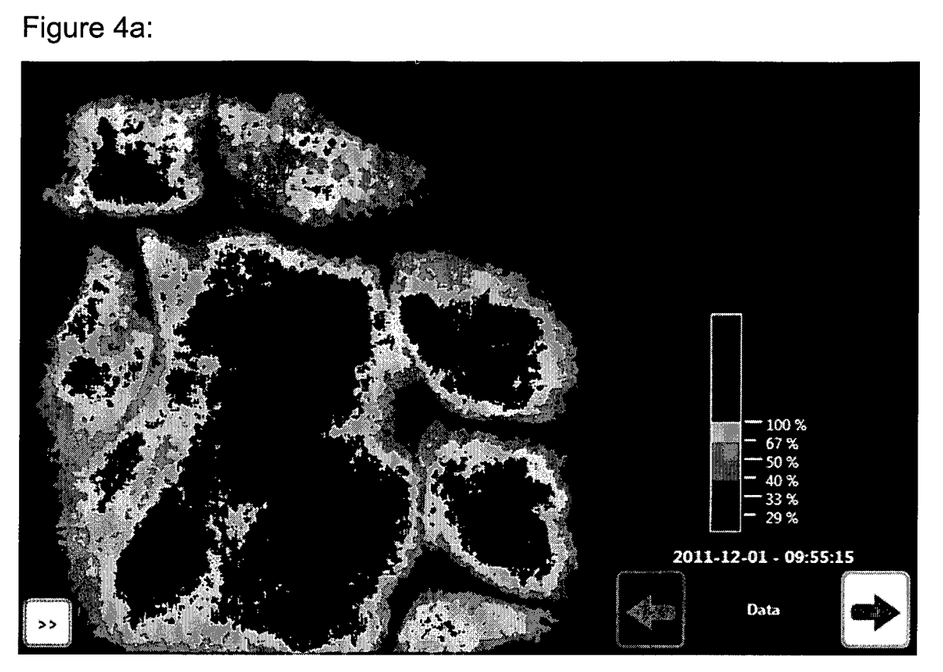
FIG. 4*a*: Example of a Colormap where only Relative Perfusion Values (of an area of a left hand) in the range from 29% to 100% are displayed (different shades of blue), while the other Relative Perfusion Values are not displayed (set to black).
Figure 4B:
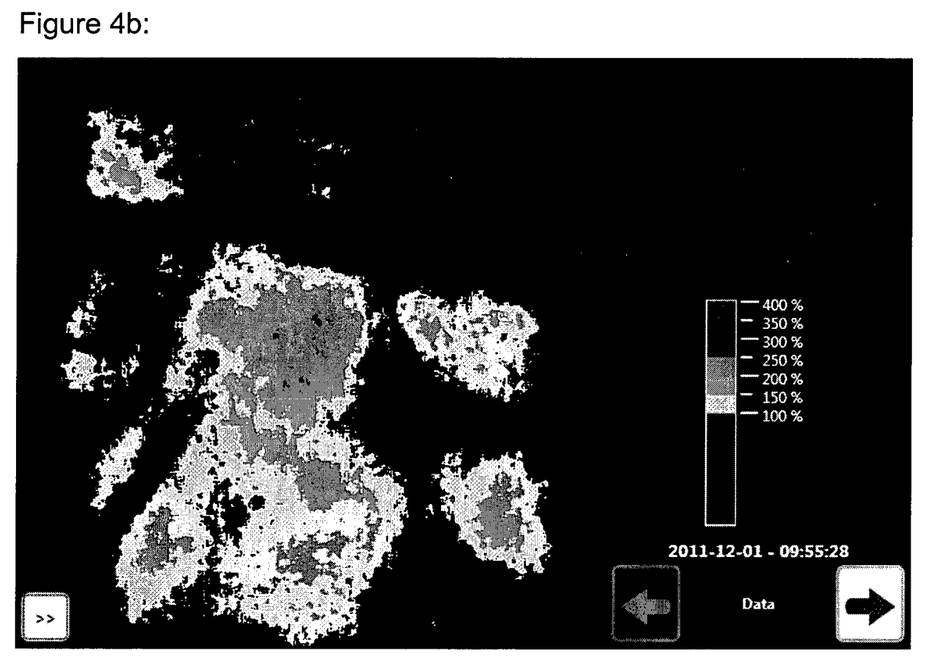
FIG. 4*b*: Same example as in FIG. 4*a*, except that here the Relative Perfusion Values between 100% and 400% are displayed (colors from yellow via red to pink), while the other Relative Perfusion Values are not displayed (set to black).

In most cases value$_{rel}$(x, y) has to be mapped to a fixed (unsigned) integer value to be usable as (indexed color) image. Often not the full range can be mapped to integer values because the range of the integer is limited (e.g. 255, thus the range of the Relative OCI Value to be used has to be defined. Ranges depend on the imaging case and the clinical need. Usual ranges are from 25% to 400% or 33% to 300%. Ranges don't have to be centered with regard to 100%, for example for Burns application a reasonable range is 50% to 300%. Depending on the clinical need, various linear and non-linear mapping functions can be used while the >100% range and the <100% range can be mapped differently. Examples are given in FIGS. 2a and 2b. For a simplified calculation the mapping with curve can be approximated through several linear segments. In the preferred embodiment it was found that an Indexed Map with 8-bit integer values which corresponds to 255 colors is sufficient for most clinical applications.

Colormap

The Indexed Map can be converted to a color image by applying a Colormap. It can be useful to use different Colormaps for Relative OCI Maps and Absolute OCI Maps to allow the user to more easily verify the imaging mode and thus reduce potential risks related to a possible misinterpretation of OCI Maps or OCI Values. The range of OCI Values mapped to colors can be set so that it is clinically most useful and makes the relevant information easily visible (e.g. [50%; 300%], or [150%; 250%], or [25%; 75%], or [12apu; 43apu]), and can be combined of multiple segments (e.g.

[50%; 100%] ∪ [150%; 200%]). The visualization of an OCI Map can then be configured that OCI Values outside the range of the Colormap have a specific color (e.g. black) or are set transparent. Consequently, the Colormap can also define that specific OCI Values are transparent or represented in a specific color (e.g. blue to white to red mapping; JET map or other mappings) Different segments can have different colors.

In the field of burn depth assessment using the Relative Mode, a well-working Colormap is blue-white-red with blue used for Relative Perfusion Values clearly below 100% and red used for Relative Perfusion Values clearly above 100%. White is used for Relative Perfusion Values around 100%. Red and Blue have a gradient of saturation between the White center region and the extremes.

Overlaying OCI Maps on White Light Images

Figure 5A:
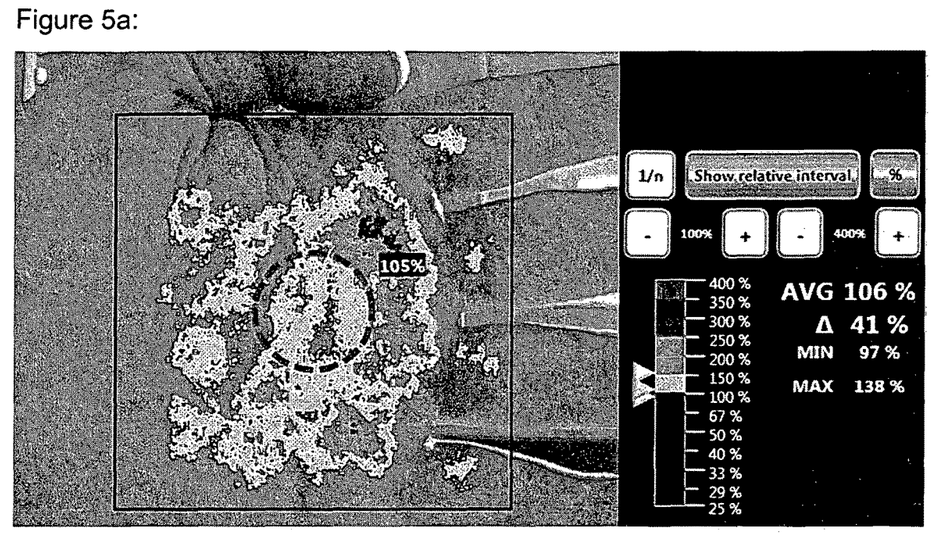
FIG. 5*a*: Example of a Colormap where only Relative Perfusion Values (of a left hand) in the range from 100% to 400% are displayed, while the other Relative Perfusion Values are set transparent so that the underlying white light image becomes visible.
Figure 5B:
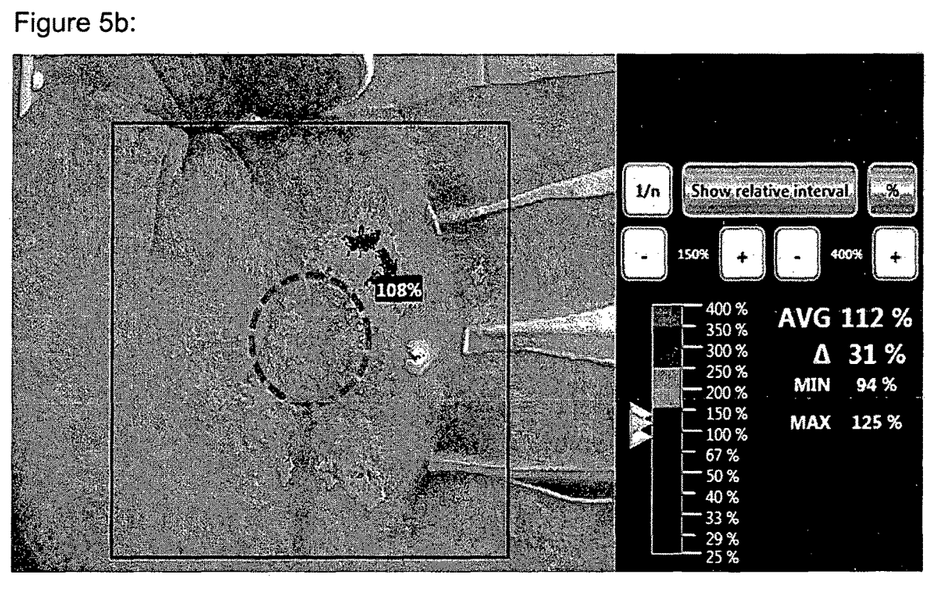
FIG. 5*b*: Same example as in FIG. 5*a*, except that here the Relative Perfusion Values between 150% and 400% are displayed (colors from yellow via red to pink), while the other Relative Perfusion Values are set transparent so that the underlying white light image becomes visible.

The projection of an OCI Maps over a white light image produced with a regular digital color camera create a combined view that allows a user to more easily localize the areas with a particular perfusion level. This technique can be used with any Colormap, but it is particularly interesting to use the technique with selective Colormaps that filter particular perfusion levels and paint it with a particular color (or a set of colors). Thus, such a painted area, when it is projected over the white light image, explicitly shows the limits of a zone with the corresponding perfusion level on the patient's skin. Other Perfusion Values can be removed and shown transparently. FIGS. 5a and 5b show two examples of such combined visualizations.

Combined Relative and Absolute Mode

In some applications it can make sense to combine elements from the Absolute Mode with elements from the Relative Mode. An example is to show Absolute OCI Maps and to combine this with the calculation of Relative OCI Values in one or several Regions of Interest. Both the Absolute OCI Values and the Relative OCI Values of the ROI can then be displayed and/or stored as numeric values or in any other suitable form. On top, the scaling of the Absolute OCI Map or the Colormap used to show the Absolute OCI Map can be a function of the Reference OCI Value (e.g. by scaling such that the Reference OCI Value as a specific color). It is not required to do the Relative calculation (as indicated in Equation 1) on the full OCI Map, but the calculation can also be done on a few OCI Values only.

Storing Reference Values and Meta Data

Usually the Reference OCI Value is used within a single session and a new reference value is taken in a new session, even if the patient doesn't change. In most scenarios, it is however useful to store the Reference OCI Value for documentation purposes or for future reuse in a new imaging session.

Therefore it can make sense to store the Reference OCI Value both as an individual dataset, but also linked to or merged with each OCI Map that uses the said Reference OCI Value. In the same spirit, it can also be useful to store information on the location of the body area, the selected Patient Population and Clinical Context, and any other relevant information, both for documentation, reverse calculation and post-analysis purposes.

Offline Processing

The whole Relative Mode approach is described for online or real-time processing, but it can also be implemented for offline processing. In offline processing the OCI Data is stored and processed later for Relative Mode calculation, probably with a separate computer system. Many workflows are possible including taking reference with the OCI device, calculating reference from a stored OCI map, running two separate OCI systems where OCI maps are transferred to the second system on which the relative assessment is calculated, etc.

Reference OCI Value within the same OCI Map

It is also possible to take the Reference OCI Value from the same OCI Data as the one that is used for imaging. In such a workflow, the user or an automated algorithm selects an ROI within an OCI Map and uses the Reference OCI Value calculated from this ROI to calculate Relative OCI Values or a Relative OCI Map of said OCI Map. This method preferably works with OCI systems that have larger imaging areas, and can use using offline processing.

ROI Values in Relative OCI Maps

Care must be taken when calculating a ROI Value from Relative OCI Map, because the mapping from Absolute to Relative OCI and/or the mapping from Relative OCI Value to Indexed Map is often not linear, which can falsify mean value calculations. This can be corrected by several methods (but not limited to): Instead of using the mean value, the median value can be used. In this case, the ROI Value is still correct because the mapping from Absolute to the Relative OCI Value usually is continuous. Another method would be to calculate the ROI Value on the Absolute OCI Map, and then convert the ROI Value to a Relative OCI Value by using the same function and parameters used to calculate the said Relative OCI Map.

Body Mapping Factors

The inventors have discovered that while the baseline Absolute Perfusion Values of tissue differs among body areas of an individual patient and within different patients, the ratio of the Absolute Perfusion Values between the body areas of an individual patient is similar within a Population Group. These ratios are called Body Mapping Factors.

A Body Mapping Factor describes the relationship of the base perfusion between two body areas. The general relationship is given in equation (3). Often the relationship can be described as a simple factor as shown in function (4) where the Perfusion of Area B is calculated from Area A for a Population X with the ratio $Factor_{AB,X}$. The factor is mostly dependent by the two areas, the Population Group and the Clinical Context.

$$Value_B = f_{AB,X}(Value_A) \tag{3}$$

$$Value_B = f_{AB,X}(Value_A) = Value_A \cdot Factor_{AB,X} \tag{4}$$

In that case the Factor to get the opposite direction is also the inverse of the ratio as shown in equation (5). In the general case this relationship is given with the function $f_{BA,X}(\ )$.

$$Factor_{BA,X} = \frac{1}{Factor_{AB,X}} \tag{5}$$

The equation (4) can also be extended with an $Offset_{AB,X}$ for some cases of perfusion relationships.

Not all relations between body areas are necessary statistically significant. Thus the Body Mapping Factor doesn't necessary exist for all pairs of body areas. Typically, the Body Mapping Factor is calculated on the baseline Absolute Perfusion Values of a given Population Group in a defined Clinical Context.

The Intra-Individual Relative Assessment as introduced before may be used in certain clinical settings to compare the perfusion between different body areas, whether healthy or injured. The result of such assessment can be misleading because the baseline Perfusion of the two body areas can differ. The Body Mapping Factor for a given pair of body areas and a given Population Group can be used as correction factor to improve the clinical relevance of the Intra-Individual Relative Assessment, such process being called Body Mapping Correction.

This principle of Body Mapping Correction can be applied to any OCI Value, given that the used Body Mapping Factor is known and meaningful in the given Clinical Context. The Body Mapping Factors can be applied to the Relative OCI Values or to its 1/x inverse, and/or it can be applied to the reference. The Body Mapping Factor can be applied to a displayed Absolute or Relative ROI Value (as numbers, gauge indication or similar) and/or to the OCI Map as such. Another option is to keep the OCI Data untouched, but change the labeling and/or the Colormap.

Figure 9:
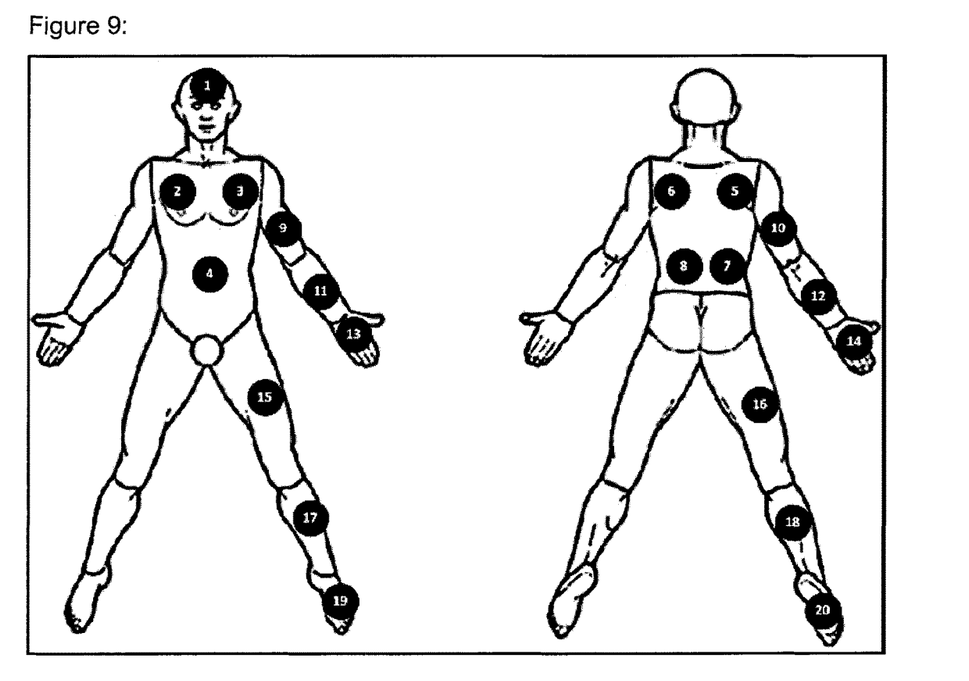
FIG. 9: Body parts used for Burns Mode (Example). List of body parts used: (1) forehead, (2) chest—right side, (3) chest—left side, (4) abdomen—center, (5) upper back—right side, (6) upper back—left side, (7) lower back—right side, (8) lower back—left side, (9) upper arm—ventral, (10) upper arm—dorsal, (11) forearm—ventral, (12) forearm—dorsal, (13) hand—palm, (14) hand—dorsal, (15) thigh—ventral, (16) thigh—dorsal, (17) lower leg—ventral, (18) calf, (19) foot—ventral, (20) foot—dorsal.

The level of granularity required for the segmentation of the body areas relevant to the Body Mapping Factors depends on the Clinical Context and the clinical goals. Usually the Body Mapping Factors are taken from healthy skin. In the field of burn depth assessment, the preferred embodiment currently uses the body areas as described in FIG. 9. In other applications, the granularity might have to be much more detailed, and potentially also limited to certain zones of a patient. Eventually, Body Mapping can also be done on and across different organs such as skin, inner organs, bones and other perfused tissues. Also, in some clinical settings it might be useful to look at OCI Values in response to a defined stimulation protocol (e.g. heating, occlusion, medication).

Body Mapping allows the use of different body areas and to compare their perfusion with statistically known relationship. Also, Intra-Individual Relative Assessment in combination with Body Mapping Factor allows extending the assessment to compare Perfusion for different patients thus extending the Inter-Individual Relative Assessment to a Relative Assessment between patients. Body Mapping Factors can be used to identify certain risks or disease stages, as well as a correction factor when the Reference Zone differs from the Imaging Zone.

Just from the way Body Mapping Correction works and Body Mapping Factors are defined, Body Mapping Factors automatically involve Intra-Individual Relative Assessment.

Body Mapping Factor Tables

The collection of Body Mapping Factors relevant to a Population Group and a Clinical Context is referred to as Body Mapping Factor Table. One or several Body Mapping Factor Tables can be combined to a Body Mapping Factor Database. This wording shall not limit the way the Body Mapping Factors are stored or accessed in the system. Any database, tables or other reasonable file/data structure and logic can be used to store the Body Mapping Factors or to calculate them from some other data structure. It is only necessary that the system can look up the Body Mapping Factors based on Clinical Context, Population Group, Reference Zone and Imaging Zone. The database can be stored on the OCI system or somewhere else and be accessed by the device when needed. Such access can also be accomplished through network, Internet or any other data transport means. Independent of the physical location the Database is considered as part of the device. Also, the Database can be updated with new and potentially improved and/or extended Body Mapping Factors over time.

Some Body Mapping Factors can be statistically more significant than others within the same Population Group or Clinical Context. The Database can therefore be extended with additional parameters providing reliability information for each Body Mapping Factor (or a group of Body Mapping Factors). In such a case, the OCI system might display the reliability information, automatically disable Body Mapping Correction, ask the user to select a different Reference Zone/Value, or use the reliability information for any other means to improve the clinical value and reduce the risk of misinterpretation.

Population Groups

Perfusion can be influenced by wide range of factors including, but not limited to, skin pigmentation, age, nutrition, gender, temperature, medication, injuries (e.g. wounds, vascular blockages), diseases (e.g. cardiovascular diseases, certain forms of rheumatology, diabetes), and others. When defining Population Groups, influencing factors should be taken into account which would change the Body Mapping Factor. For example a Population Group could be males in the age of 25 to 40 years or diabetic women aged older than 60 years. Typically, Population Groups are specifically designed for a specific clinical application of the OCI system.

In some Clinical Context it is possible that a differentiation of Population Group is not needed. In such case this parameter for lookup of the Body Mapping Factor is obsolete and any workflow step for selecting the Population Group can be skipped. The Body Mapping Factor Database then only contains a single Body Mapping Factor Table for the given Clinical Context.

Body Mapping Studies

Figure 6:
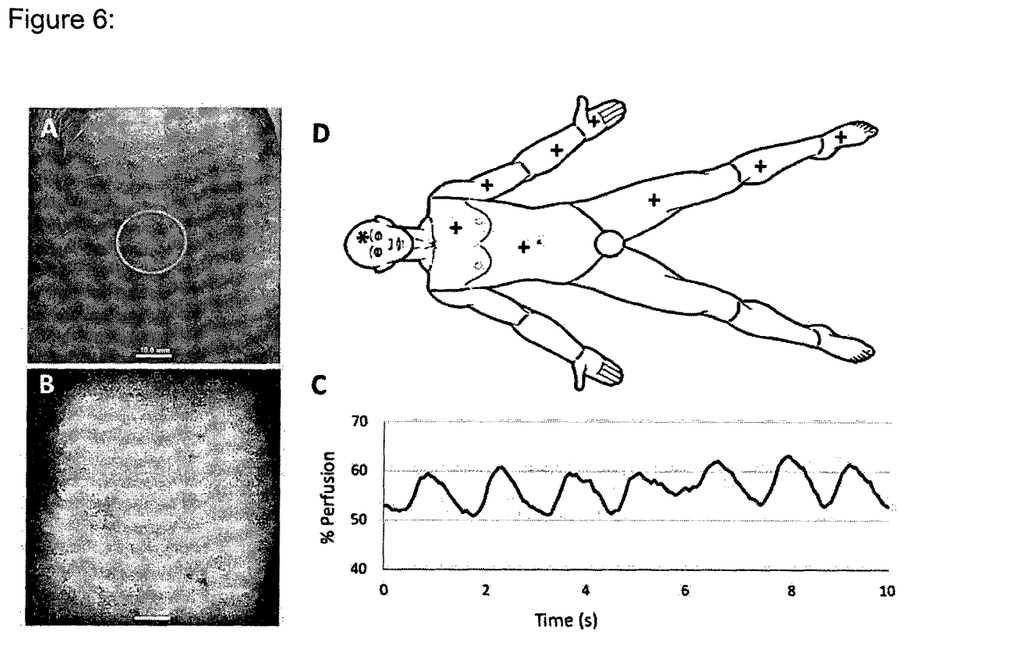
FIG. 6: Measurement procedure as used in the Body Mapping study. A: Color photograph (forehead) with an ROI area, B: LDI image with the same ROI area, C: Plot of measured Relative Perfusion Values within an ROI over time, D: Locations for measurement points on the body, where (+) stands for measurement locations on both the ventral and dorsal side, while (*) indicates measurement on ventral side only.
Figure 7:
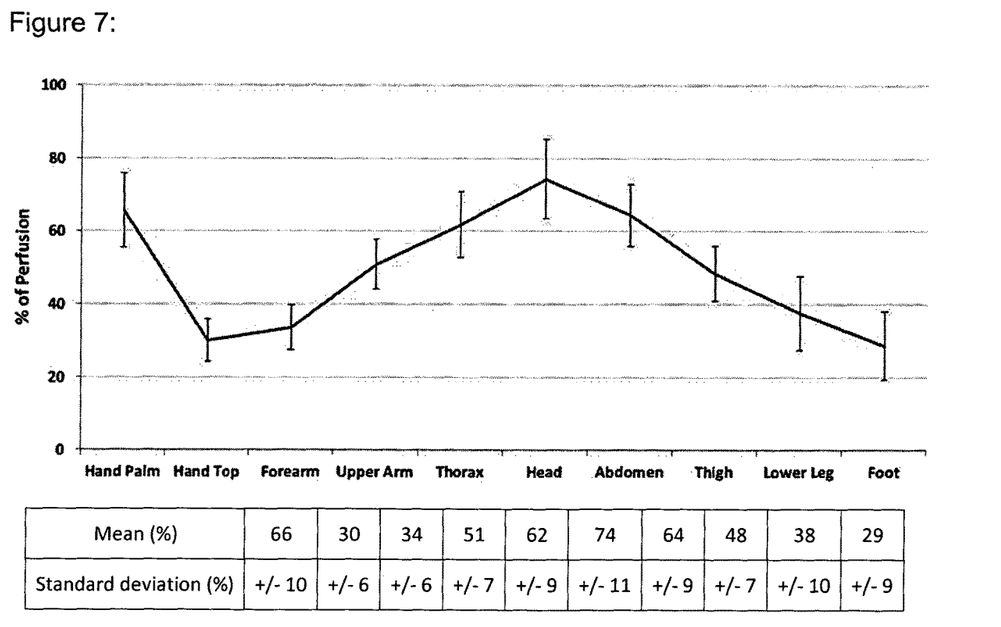
FIG. 7: Mean and standard deviation of data of Body Mapping study after regrouping into 10 groups, pairing ventral and dorsal data sets for all body regions except for the hand.
Figure 8:
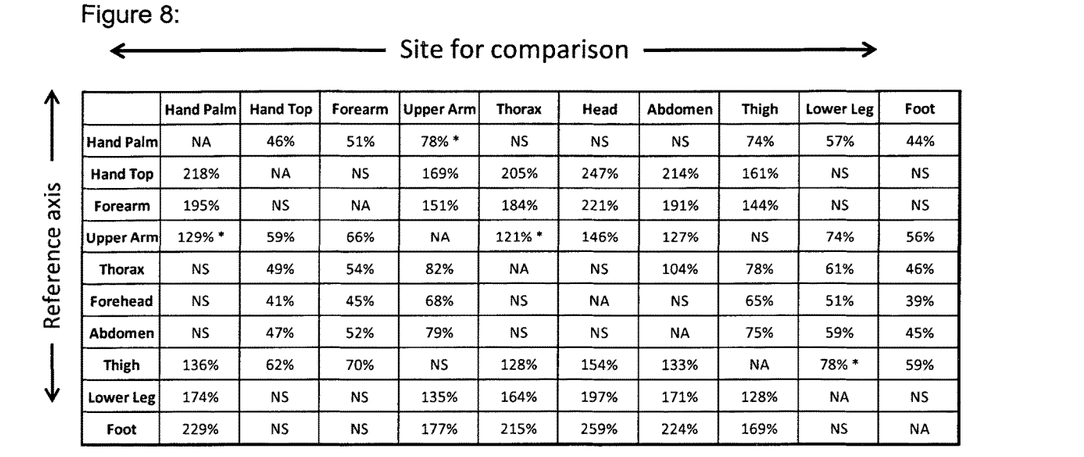
FIG. 8: Body Mapping Factor Table as found in the study. As example the average perfusion of the forearm of a healthy patient ("reference" axis) should be multiplied by a factor of 2.21 to predict the perfusion on the forehead of the same patient ("site for comparison" axis).

The inventors have so far performed two small studies related to the Body Mapping concept. The data presented in FIGS. 6 to 8 are taken from the first study, and have been confirmed by the second study. Further studies are required to develop and fill the Body Mapping Factor Databases for specific Clinical Context and Population Groups.

In the first study, eight healthy individuals were imaged on 17 body areas as indicated in FIG. 6D. At each of these body areas, 10-second videos of LDI based Absolute Perfusion Maps (FIG. 6B) were recorded along with the corresponding white light photograph for future location identification (FIG. 6A). For each video sequence, a ROI was manually defined and applied to the same area for all images in the video sequence. Next, the average Absolute Perfusion Value of the ROI was plotted versus time (FIG. 6C). Here, microcirculatory pulsations can be seen and average perfusion can be calculated for the defined sequence. Any large variations due to patient movement from the normal pulsation profile, for example, can be easily identified, thus indicating that this perfusion video is not valid and a new sequence should be recorded. The ROI Values were segmented into 10 groups, pairing ventral and dorsal data sets for all body regions except for the hand. The mean and standard deviations of this data is shown in FIG. 7. Next, ANOVA statistical analysis, followed by the Tukey test was performed again on the regrouped data (FIG. 7) to test which data pairs have a significantly different interaction. All significantly different data pairs and their corresponding mean ratios are shown in FIG. 8 ($p<0.01$, *$0.01<p<0.05$). To use this data practically, FIG. 8 indicates that the average perfusion of the forearm of a healthy patient ("reference" axis) should be multiplied by a factor of 2.21 to predict the perfusion on the forehead of the same patient ("site for comparison" axis). These types of regional relations can be made at all intersections of the x and y axis of FIG. 8, with the percentage value indicating the interaction specific correction factor. It was shown that although Absolute Perfusion may vary among patients, intra-individual perfusion ratios between body regions are significantly distinguishable from one another. Of the 10 independent data sets analyzed, there are possibilities to have 45 total independent data pair interactions. It was demonstrated that at least 32 of the 45 possible pairs are significantly different from one another and included the corresponding ratios of their means in FIG. 8. What makes these results particularly interesting are they indicate that, although as individuals we may have varying degrees of Absolute Perfusion, when considering the same body regions, the relative intra-individual ratios of perfusion between body regions are in fact very similar.

Section of Body Area and Population Group

Selecting the body area (Imaging Zone or Reference Zone) is normally done by the user through the human machine interface of the OCI device. In case with a touch screen, clicking on the body part can do this when an outline of a patient's body is shown (see FIG. 9 with an example). It can also be done using selection from a list, entering a body part code or any other reasonable means. Required accuracy for selection depends on the granularity of the body areas in the Body Mapping Factor Database. Other embodiment is possible where the body part is automatically or semi-automatically detected. This can be achieved by means of a navigation system knowing the coordinate and orientation of the OCI system and patient; image recognition; reading of pre-labeled tags on the patient; or any other methods.

Similarly, the selection of the Population Group can be done manually by the user through the Human Machine Interface and/or some criteria can be automatically detected by the system with appropriate sensors and means.

Information on the body area used, Body Mapping Factors, Databases and/or Population Groups and references thereof can be stored, preferably together with the OCI Data, both for the purpose of documentation or further analysis and reverse calculations.

It is also possible to allow the user to enable/disable the Body Mapping Correction, thus allowing the usage of the device without applying the Body Mapping Factor. In the same spirit it is possible to show the corrected and uncorrected results to the user at the same time.

Device

Figure 1:
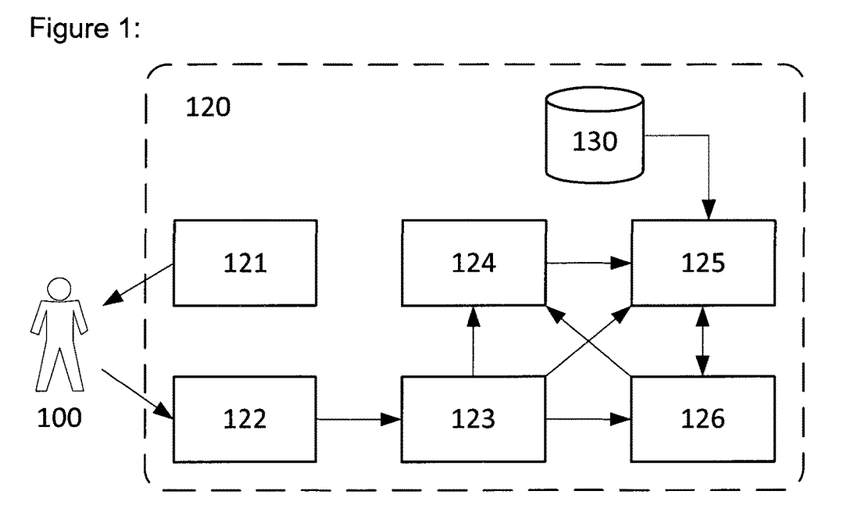
FIG. 1: A block diagram of a preferred embodiment of an OCI device including Intra-Individual Relative Assessment: (100) Patient, (120) OCI device, (121) coherent light source, (122) light sensor, (123) processing unit to calculate OCI Maps, (124) control unit to take or load OCI Reference Value, (125) processing unit to calculate Intra-Individual Relative Assessment, (126) Human Machine Interface.

A preferred embodiment of a device which implements Intra-Individual Relative Assessment is shown in FIG. 1.

A coherent light source (121), usually a Laser source in the visible or near-infrared wavelength illuminates the area of interest on the subject (100). Such illumination can be done with optics for full-field illumination such as lenses or diffractive elements, by mechanically scanning a single point or line, or by other suitable means. A light sensor (122) captures the reflected light. Such light sensor can be a single photo diode, a CCD, non-integrating or integrating CMOS sensor or any other sensor technology for capturing the light and transferring it to an electronic signal. The sensor often is a 2D array of pixels. The light sensor may contain other optical elements such as lenses, mirrors, filters, prism, scanning mechanics or other means to transform the light as needed and to convert it into a two dimensional data. An OCI processing unit (123) controls the coherent light source and the light sensor and calculates one or multiple Absolute OCI Maps or Absolute OCI Values from the signal of the light sensor. The timing and whether first all pixels of the map are read and the processed or if a group of pixels is processed at the time depends on the implementation. In the example of LDI such processing normally involves calculating the power spectrum for each pixel in time and calculating the zero and/or first momentum of the power spectrum. The OCI processing unit can also include filters and other means to improve the signal quality. The OCI processing unit can be implemented in a FPGA, a CPU, a GPU, a DSP, a combination of those, or any other reasonable processing means.

In another embodiment with Laser Speckle Contrast Analysis (LASCA) or Laser Speckle Imaging (LSI), the processing unit (123) can be built such that it calculates the contrast of the detected light in space and/or time and derives an OCI map from it. Similarly other OCI technology can be used to calculate the OCI map. The details of OCI map calculation is known to those skilled in the art. The details of the implementation of the OCI technology shall not limit this patent application.

To perform Intra-Individual Relative Assessment a Reference OCI Value must be taken or loaded which is done in the preferred embodiment by a Reference control unit (124). In the preferred embodiment the user can control the Reference Zone, the ROI and the time when the Reference OCI Value is taken with the Human Machine Interface (HMI). The Reference control unit captures one or several OCI maps from the OCI processing unit at this time and calculates the ROI Value from the OCI maps as Reference OCI Value. This process may involve time or spatial filter and/or other means. It is usually preferable to remove the pulsation from the heart beat with such filters. It may also be possible that the user can load the Reference OCI Value from a file or other storage instead. In another embodiment an algorithm automatically decides the Reference Zone and calculates the Reference OCI Value accordingly. In any embodiment it is possible to set and calculate multiple Reference OCI Values including a full Reference OCI map.

A Relative processing unit (125) uses the Reference OCI Values and the OCI maps from the OCI processing unit to calculate Relative OCI Values and/or Relative OCI maps. The preferred implementation is a simple division of the OCI Values with the Relative OCI Value and a mapping to an integer value which includes scaling to specific range. The Relative processing unit can be implemented in a FPGA, a CPU, a GPU, a DSP, a combination of those or any other reasonable processing means. It is also possible to combine the OCI processing unit and the Relative processing unit in a single unit. It is also imaginable to combine the Reference control unit with one or both of the processing units.

In some embodiments a Body Mapping Factor Database (130) is included or connected. In such embodiment the Population Group information is given by the user through the Human Machine Interface or it is automatically determined. The Reference processing unit selects the correct Body Mapping Factor Table and uses the Body Mapping Factor to adjust the Relative OCI Value. Reference Zone and Imaging Zone are also adjusted through means of the Human Machine Interface or automated detection. Of course the Body Mapping Factor algorithm can also be separated in a separate processing unit or combined with another unit.

The result is output to the user through the Human Machine Interface (126). The same interface can also be used to show the Absolute OCI maps from the OCI processing unit. The Human Machine Interface is preferably implemented with a Touch Screen and/or physical buttons. A classic computer interface (keyboard, mouse, display) is possible as well. It is also possible to have several displays, a printer, or output to files.

EXAMPLE 1

Burns Healing Assessment

Figure 10:
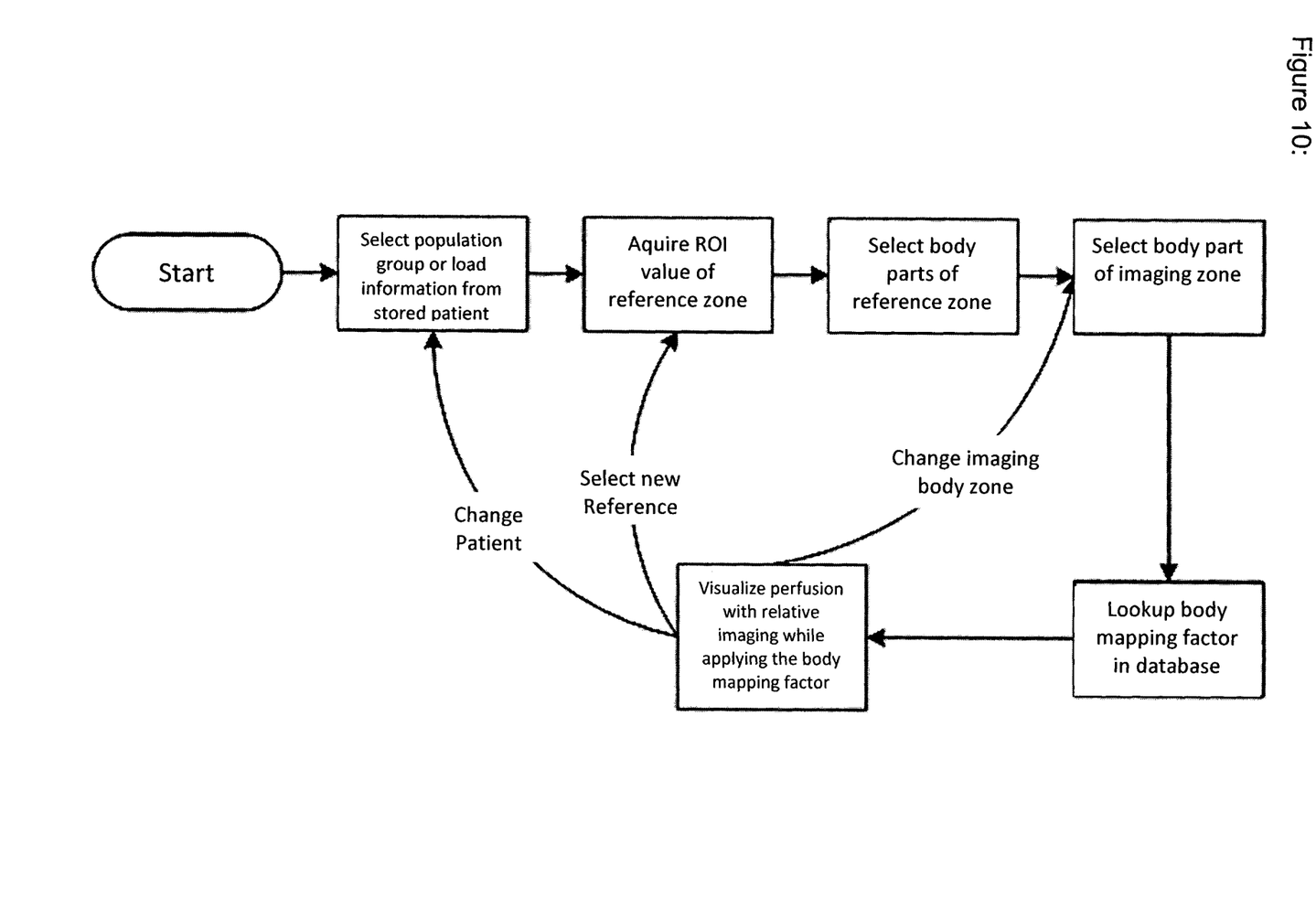
FIG. 10: Example workflow for burn depth assessment using the Body Mapping Factor.

A workflow example is given for using Body Mapping Correction in the LDI based assessment of the healing potential of partial thickness burn wounds (see also FIG. 10). The principle here is to understand which parts of the burn wound are subject to an inflammatory response and thus hyperemic compared to equivalent skin at the same body area.

1. Ask the user for the Population Group and then select the relevant Body Mapping Factor Table based on the Population Group (i.e. by taking age, skin pigmentation and comorbidities into account) and the Clinical Context (i.e. burn depth assessment). The information may be stored in the patient file.
2. Take a Reference OCI Value on healthy skin. The device asks the user to select the body area where the reference is taken.
3. The user is asked to select the body area where burn wound to be evaluated is located (Imaging Zone). If it is the same body area where the reference has been taken, then Body Mapping Factor is 1, otherwise the Body Mapping Factor is looked-up in the Body Mapping Factor Database.
4. The Relative Perfusion Values and Relative Perfusion Maps shown and recorded are corrected using the Body Mapping Factor.
5. The steps 2-3-4 and 3-4 can be repeated at the user's discretion.

A very similar workflow can be used for flap viability assessment as well.

EXAMPLE 2

Peripheral Vascular Disease (PVD) Assessment

A workflow example to identify and evaluate extremity perfusion impairment and post-interventional hyperemic response by comparing the forehead to extremity perfusion ratio with an appropriate Population Group without PVD is provided:

1. Ask the user to select the Population Group, and then select the relevant Body Mapping Factor Table based on the Population Group (i.e. by taking comorbidities into account) and the Clinical Context (i.e. PVD).
2. Take a Reference OCI Value (e.g. with LDI) on healthy skin (i.e. the forehead). The device asks the user to select or automatically sets the body area where the reference is taken.
3. The user is asked to select the body area of the extremity to be evaluated, and the Body Mapping Factor is looked-up in the Body Mapping Factor Database to set the expected baseline perfusion level for the given Population Group.
4. The (Relative) Perfusion Values and (Relative) Perfusion Maps shown and recorded are corrected using the Body Mapping Factor.
5. The steps 2-3-4 and 3-4 can be repeated at the user's discretion.

The above-mentioned workflows are just examples and can be modified or optimized. Also, other workflows can be specified for these or other clinical applications. It is also possible to use the Body Mapping Factor to set minimum and maximum perfusion for a given body part from a statistical reference group. This Perfusion (Absolute or Relative) can then be used to check for a given patient if the perfusion is in the "good" range.

Most workflow include in some way the selection of a Population Group, a Body Mapping Factor Database, the acquisition of a Reference OCI Value and selection of Imaging Zone body areas needed to look-up the Body Mapping Factors in the Database.

The invention claimed is:

1. An optical coherent imaging (OCI) medical device for imaging the tissue of a subject comprising:
a coherent light source configured to illuminate an imaging zone of the subject;
a light sensor with a two-dimensional array of pixels configured to capture an image from the imaging zone;
a first processing unit configured to process data received from the light sensor and calculate Absolute OCI Data corresponding to blood flow in the imaging zone;
a control unit which allows taking or loading of at least one Reference OCI Value associated with blood flow in a body part spaced from the imaging zone;
a second processing unit adapted to calculate Relative OCI Data, said Relative OCI Data being proportional to perfusion, velocity and/or concentration of the blood flow in the imaging zone, said Relative OCI data being calculated based on the calculated Absolute OCI Data from the imaging zone modified by the at least one Reference OCI Value and wherein the calculation is based on one of (a) a division of the Absolute OCI Data with the at least one Reference OCI value and (b) a difference between the at least one Reference OCI value and the Absolute OCI data; and
a display adapted to show the calculated Relative OCI Data.

2. The device according to claim 1, wherein said two processing units are forming a single processing unit.

3. The device according to claim 1, which is adapted for performing Laser Doppler Imaging (LDI).

4. The device according to claim 1, which is adapted for performing a Laser Speckle Contrast Analysis (LASCA) or Laser Speckle Imaging (LSI).

5. The device according to claim 1, further comprising a Body Mapping Factor Database including body mapping factor values for a population group, wherein each of the body mapping factor values represents a relationship of OCI values between two body areas for the population group.

6. The device according to claim 5 where the body mapping factor values are calculated based on the ratio of the OCI Values between two body areas.

7. A method for assessing the blood flow of a body region using optical coherent imaging (OCI) comprising;
illuminating an imaging zone in the body region with coherent light from a coherent light source;
capturing an image from the imaging zone with a light sensor having a two-dimensional array of pixels;
calculating in a processor Absolute OCI Data from the captured image data corresponding to blood flow;
capturing or loading at least one Reference OCI Value associated with blood flow in a body part spaced from the imaging zone;
calculating in the processor Relative OCI Data, said Relative OCI data being proportional to perfusion, velocity and/or concentration of the blood flow in the imaging zone, said Relative OCI data being calculated based on the calculated Absolute OCI Data from the imaging zone modified by the at least one Reference OCI Value and wherein the calculation is based on one of (a) a division of the Absolute OCI Data with the at least one Reference OCI value and (b) a difference between the at least one Reference OCI value and the Absolute OCI data; and
displaying the Relative OCI Data on a display.

8. The method according to claim 7, further comprising using a Body Mapping Factor Database including body mapping factor values for a population group, wherein each of the body mapping factor values represents a relationship of OCI values between two body areas for the population group.

9. The method according to claims 7, wherein the at least one Reference OCI Value is obtained or filtered such that pulsations of the heart beat are removed.

10. The device according to claim 1, wherein the device is used to assess burn wounds or flap viability.

11. The device according to claim 1, wherein the device is used to assess systemic vascular issues.

12. The device according to claim 1 wherein the device is used to assess ulcers or bedsores.

13. The device according to claim 5, wherein the control unit is configured to select the body mapping factor value based on the locations of the imaging zone and the body part spaced from the imaging zone and modify the Relative OCI Data with the selected body mapping factor value.

14. The device according to claim 1 wherein the calculation of a Relative OCI Value is performed for each pixel in the Absolute OCI Data.

15. The method according to claim 8 further comprising:
selecting the body mapping factor value representing the relationship of the OCI values between two body areas for the population group based on the locations of the imaging zone and the body part spaced from the imaging zone and modifying the Relative OCI Data with the selected body mapping factor value.

16. An optical coherent imaging (OCI) medical device for imaging the tissue of a subject comprising:
a coherent light source configured to illuminate an imaging zone of the subject;
a light sensor with a two-dimensional array of pixels configured to capture an image from the imaging zone;
a first processing unit configured to process data received from the light sensor and calculate Absolute OCI Data corresponding to blood flow in the imaging zone;
a control unit which allows taking or loading of at least one Reference OCI Value associated with blood flow in a body part spaced from the imaging zone;
a second processing unit adapted to calculate Relative OCI Data, said Relative OCI Data being proportional to perfusion, velocity and/or concentration of the blood flow in the imaging zone, said Relative OCI data being calculated based on the calculated Absolute OCI Data from the imaging zone modified by the at least one Reference OCI Value;
a Body Mapping Factor Database including body mapping factor values for a population group, wherein each of the body mapping factor values represents a relationship of OCI values between two body areas for the population group and wherein the control unit is configured to select the body mapping factor value based on the locations of the imaging zone and the body part spaced from the imaging zone and modify the Relative OCI Data with the selected body mapping factor value; and
a display adapted to show the modified Relative OCI Data.

17. A method for assessing the blood flow of a body region using optical coherent imaging (OCI) imaging comprising;
illuminating an imaging zone in the body region with coherent light from a coherent light source;
capturing an image from the imaging zone with a light sensor having a two-dimensional array of pixels;
calculating in a processor Absolute OCI Data from the captured image data corresponding to blood flow;
capturing or loading at least one Reference OCI Value associated with blood flow in a body part spaced from the imaging zone;
calculating in the processor Relative OCI Data, said Relative OCI data being proportional to perfusion, velocity and/or concentration of the blood flow in the imaging zone, said Relative OCI data being calculated based on the calculated Absolute OCI Data from the imaging zone modified by the at least one Reference OCI Value;
using a Body Mapping Factor Database including body mapping factor values for a population group, wherein each of the body mapping factor values represents a relationship of OCI values between two body areas for the population group and selecting a body mapping factor value based on the locations of the imaging zone and the body part spaced from the imaging zone and modifying the Relative OCI Data with the selected body mapping factor value; and
displaying the modified Relative OCI Data on a display.

* * * * *